United States Patent [19]

Covill et al.

[11] 4,395,566

[45] Jul. 26, 1983

[54] SOLVENT-FREE ESTERIFICATION OF CARBOXYAROMATICS

[75] Inventors: James H. Covill, Pineville, N.C.; Michael G. Kelly, Coventry; Thomas F. Leahy, E. Greenwich, both of R.I.

[73] Assignee: American Hoechst Corporation, Somerville, N.J.

[21] Appl. No.: 355,812

[22] Filed: Mar. 8, 1982

[51] Int. Cl.$^3$ .............................................. C07C 67/08
[52] U.S. Cl. ...................... 560/87; 544/388; 544/406; 546/170; 546/326; 546/327; 548/492; 549/71; 549/501; 560/11; 560/17; 560/52; 560/81; 560/84; 560/91; 560/93
[58] Field of Search ............... 560/11, 17, 81, 84, 560/87, 93, 91, 52; 260/326.13 R, 347.4, 347.5; 544/388, 406; 546/170, 326, 327; 549/71, 501; 548/492

[56] References Cited

U.S. PATENT DOCUMENTS

| | | | |
|---|---|---|---|
| 3,870,748 | 3/1975 | Katsushima et al. | 560/87 |
| 4,134,839 | 1/1979 | Marshall | 560/87 X |
| 4,209,610 | 6/1980 | Mares et al. | 260/40 R |
| 4,252,982 | 2/1981 | Oxenrider | 560/87 |
| 4,329,489 | 5/1982 | Saunders et al. | 560/87 X |

FOREIGN PATENT DOCUMENTS 19732 12/1980 European Pat. Off. .

*Primary Examiner*—Natalie Trousof
*Assistant Examiner*—Vera C. Clarke
*Attorney, Agent, or Firm*—Stephan P. Williams

[57] ABSTRACT

An improved process for exterifying carboxyaromatics is disclosed wherein an anhydride of a carboxyaromatic, such as pyromellitic dianhydride, is reacted with a fluorinated alcohol and an expoxide to give a mixed ester capable of imparting oil and/or water repellency to textiles. The improvement comprises utilizing the expoxide as the reaction medium to reduce reaction times and waste water treatment requirements.

9 Claims, No Drawings

SOLVENT-FREE ESTERIFICATION OF CARBOXYAROMATICS

BACKGROUND OF THE INVENTION

This invention relates to the esterification of carboxyaromatics, particularly through the reaction of an anhydride of a carboxyaromatic with a fluorinated alcohol followed by reaction of the resulting ester/acid with an epoxide. Such an esterification process is generally known, especially in the preparation of compounds capable of imparting oil and/or water repellency to textiles such as polyester and nylon fibers.

In particular, U.S. Pat. No. 4,209,610 and G.B. Pat. No. 1,543,081 disclose compounds useful for imparting oil and water repellency which are prepared by contacting in solution an anhydride of a carboxybenzene and various fluorinated alcohols to form the corresponding fluorinated ester/acid, and then contacting said ester/acid in solution with an epoxide. More particularly, in Example VIII of U.S. Pat. No. 4,209,610, pyromellitic dianhydride (PMDA) is esterified in DMF with a mixture of perfluoroalkyl-ethanols to form the corresponding diester/diacid, which is then further reacted (in DMF) with excess epichlorohydrin, using a little triethylamine as catalyst, to esterify the remaining carboxyl groups to form the tetraester, which is precipitated out with ice water.

Similarly, in European Patent application No. 19,732, published Dec. 10, 1980, esterification of carboxybenzenes in N-methylpyrrolidone (NMP) solvent is disclosed and shown to be superior in comparative testing to a like product made in DMF.

In U.S. Pat. No. 4,252,982, such esterifications of carboxybenzenes are shown in aliphatic ester solvents such as butyl acetate. The use of the aliphatic ester solvents is said to overcome the waste water problem which results when DMF or NMP is employed as the solvent for such esterifications. When DMF or NMP is employed, the final product must be precipitated out with water, which takes up the solvent and thus requires waste water treatment. The advantage in using the aliphatic ester solvent is that it can be distilled from the desired product. However, the use of the aliphatic ester solvent results in a slower reaction rate, presents a flammability hazard, and produces a slightly inferior product in comparison with the NMP process.

SUMMARY OF THE INVENTION

Applicants have discovered an improved process for the esterification of carboxyaromatics by fluorinated alcohols and epoxides which results in substantially faster reaction times and substantially reduced waste water treatment requirements when compared with presently known processes. Applicants' improved process also results in a product which is comparable in quality to one produced in NMP, which is known to be superior to the like product produced in DMF or aliphatic ester solvent.

Applicants have discovered that the process for the esterification of a carboxyaromatic by reacting an anhydride of said carboxyaromatic with a fluorinated alcohol and then an epoxide can be improved by utilizing the epoxide as the solvent or reaction medium for the esterification when said epoxide is a liquid under the reaction conditions employed.

DETAILED DESCRIPTION OF THE INVENTION

The essence of applicants' invention is the discovery that the double esterification of carboxyaromatics by fluorinated alcohols and epoxides, which has heretofore been carried out in two steps in various solvents, may be advantageously conducted in one step without added solvent when the epoxide selected for the esterification is a liquid under the reaction conditions employed. The liquid epoxide, which is normally used in excess to drive the reaction to completion, serves to keep the reaction mixture fluid and homogeneous. Thus, the applicants' process comprises intimately mixing an anhydride of a carboxyaromatic, a fluorinated alcohol, and a liquid epoxide, and heating said mixture to esterify said carboxyaromatic.

The carboxyaromatic anhydrides which can be employed in the process of this invention may be derived from any polycarboxyaromatic wherein one or more adjacent pairs of carboxyl groups have been converted to the anhydride. The carboxyaromatics of general interest are the one and two ring aromatics such as benzene, naphthalene, pyridine, pyrazine, quinoline, indole, thiophene, furan, etc. substituted by two or more carboxyl groups, and optionally any other substituents which do not interfere with conventional esterifications. Two or more carboxyaromatics may be linked together through a chemical bond or a bridging group.

The carboxyaromatic anhydrides of choice are the anhydrides of the benzene and naphthalene carboxylic acids. Illustrative of these are the anhydrides of benzene tricarboxylic acid and tetracarboxylic acid, naphthalene tetracarboxylic dianhydride, diphenyl tetracarboxylic dianhydride, 2,2-bis (dicarboxyphenyl) propane dianhydride, 1,1-bis (dicarboxyphenyl) ethane dianhydride, bis (dicarboxyphenyl) methane dianhydride, bis (dicarboxyphenyl) sulfone dianhydride, bis (dicarboxyphenyl) ether dianhydride, and benzophenone tetracarboxylic dianhydride. Of course, anhydrides of the heterocyclic aromatics, such as pyrazine tetracarboxylic dianhydride and thiophene tetracarboxylic dianhydride, may also be employed. The preferred carboxyaromatic anhydrides are pyromellitic dianhydride (PMDA) and 3, 4, 3', 4'-benzophenone tetracarboxylic dianhydride (BTDA).

Numerous fluorinated alcohols are disclosed in the prior art, for example in G. B. Pat. No. 1,543,081, U.S. Pat. No. 4,209,610, U.S. Pat. No. 3,646,153, U.S. Pat. No. 3,547,861, U.S. Pat. No. 3,514,487, and U.S. Pat. No. 3,171,861, all of which alcohols are believed to be operative in the present process. These include fluorinated alcohols having straight chain, branched chain and cyclic fluorinated moiety attached to a hydroxy substituted hydrocarbon moiety, each moiety having between 2 and 20 carbon atoms, especially such alcohols in which the fluorinated moiety has between 3 and 12 carbon atoms and the hydrocarbon moiety has between 2 and 12 carbon atoms. The fluorinated moiety can be perfluorinated and can alternatively be partially fluorinated, for example having a terminal hydrogen atom. Also, either or both the fluorinated moiety and the hydroxyl substituted moiety can contain substituents such as chloro, bromo or iodo.

Specific suitable fluorinated alcohols for esterification of carboxyaromatics by the present process include the (perfluoroalkyl) ethanols and the (perfluoroalkyl) propanols having three to twelve carbon atoms in the perfluoroalkyl groups; and the (omega-perfluoroisopropoxyperfluoroalkyl) ethanols, and the propanol homologues thereof, having two to ten carbon atoms in the perfluoroalkyl groups. Preferred alcohols of the above group, in view of their availability and effectiveness in producing esters with the desired properties, are mixtures consisting essentially of 2-(n-perfluoroalkyl)ethanols having six to twelve carbon atoms in the perfluoroalkyl groups.

Epoxides useful in the present process are those which are liquid under the reaction conditions employed for the esterification. The preferred epoxides will provide radicals designated as "B" in U.S. Pat. No. 4,209,610. Typical of these are epoxides of the formula:

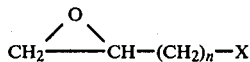

wherein n is 1 or 2 and X is hydrogen, hydroxy, halogen, or nitrile. Epichlorohydrin and glycidol are the preferred epoxides.

The process of the present invention is carried out by intimately mixing the carboxyaromatic anhydride, fluorinated alcohol and epoxide, and allowing the esterification to proceed to completion, generally at elevated temperatures. The alcohol first reacts with the anhydride to form the corresponding carboxylic acid/half ester having one fluorinated ester radical per anyhydride moiety orginally present. The free carboxyl groups formed upon opening of the anhydride (i.e. those remaining), as well as any free carboxyl groups originally present, react with the epoxide to form the corresponding ester or esters.

Generally, the fluorinated alcohol is employed in stoichiometric quantities in the present process. By stoichiometric quantities is meant that amount of alcohol which will react completely with the carboxyaromatic anhydride to give the half ester. In other words, the stoichiometric quantity of alcohol is the number of moles of carboxyaromatic anhydride multiplied by the number of anhydride groups on the carboxyaromatic anhydride. Thus, for example, one mole of alcohol reacts with one mole of a monoanhydride; two moles of alcohol react with one mole of a dianhydride, etc.

An alternative approach to defining the quantity of fluorinated alcohol employed is to say that about one equivalent of alcohol is used per equivalent of carboxyaromatic anhydride. One equivalent of alcohol is one mole. One equivalent of carboxyaromatic anhydride is one mole divided by the number of anhydride groups per molecule. Thus, one equivalent (one mole) of alcohol reacts with one equivalent (one-half mole) of dianhydride.

The epoxide is generally employed in excess quantities in order to drive the reaction to completion in a reasonable time. From a practical standpoint, it has been found desirable to use an amount which will provide a 100 to 300%, preferably a 150 to 250%, molar excess of epoxide over the stoichiometrically required amount (i.e., that amount which will react with the free carboxyl groups on the carboxyaromatic, including those formed upon esterification by the fluorinated alcohol). Thus, for example, a dianhydride such as pyromellitic dianhydride, will require about five to seven moles of epoxide to drive the reaction to completion in a reasonable time—two moles of epoxide to react with the free carboxyls formed upon esterification by the fluorinated alcohol, and three to five moles to provide the 150 to 250% molar excess needed.

The temperature and pressure employed in the present process are not critical. Their selection is based primarily on obtaining a satisfactory reaction rate while avoiding decomposition of the products. Generally, temperatures between about 40° and 60° C., give satisfactory results.

A catalyst is not necessary in the reaction of the fluorinated alcohol with the anhydride, but conventional esterification catalysts for this reaction, such as bases or Lewis acids, can be used if desired. A catalyst is helpful in the esterification by the epoxide, the organic bases being typical. Triethylamine is preferred, although pyridine and other trialkylamines may be employed.

The invention may be described in greater detail by the following examples in which the parts and percentages are by weight.

EXAMPLE 1

A dry 500 ml three-neck flask, fitted with overhead stirrer, thermometer and drying tube, was charged with 115 g of a mixture of 2-(n-perfluoroalkyl) ethanols having six to twelve carbon atoms in the perfluoroalkyl groups, 25.8 g pyromellitic dianhydride (PMDA), 1 ml triethylamine and 55.7 ml epichlorohydrin. All reactants were mixed together in the flask and the slurry heated slowly to 55° C. After 7.5 hours carboxyl titration indicated the reaction to be essentially complete and the reaction mixture was drowned into water to precipitate the product (the tetraester), which was washed to remove excess epichlorohydrin and dried under vacuum. The epichlorohydrin in the wash water was converted to glycerol by addition of sodium hydroxide.

EXAMPLE 2

Example 1 was repeated using 27.5 g PMDA and 115 g perfluoroakyl ethanol. The reaction was conducted at 45° C. and took 12.5 hours to complete.

The above products were tested for oil repellency and wash fastness in the following manner. The product was dissolved in acetone and applied onto polyester or nylon fabric through a padder. The concentration of product was adjusted so that pick up was 0.25% product compared to the weight of the fabric. After drying at room temperature, the fabric was cured (annealed) at 140° C. (nylon) or 160° C. (polyester) for 30 minutes. The fabric was then subjected to AATCC Test 61-1968 (II-A) using a launderometer from Atlas Electric Co. to simulate five home launderings at medium temperature settings. The washed fabric was evaluated for oil repellency according to AATCC Test 118-1975, the rating scale running from 0 to 8, with increasing numbers indicating greater repellency. The tested products gave oil repellency values of 5-6.

COMPARISON

The following table compares the present solvent-free process with the known esterification processes using DMF, NMP and alkyl acetate solvents according to U.S. Pat. No. 4,209,610, E.P. No. 19,732, and U.S. Pat. No. 4,252,982 respectively. As can be seen from this table, the process of the present invention produces a product (in this case, the tetraester of pyromellitic dianhydride) which is either superior or comparable to the like product produced according to the prior art processes; the present process has a substantially faster reaction time than the prior art processes; and the present process has lower waste water treatment requirements (i.e. lower BOD) than all but the alkyl acetate process which requires a difficult and hazardous distillation.

TABLE

COMPARISON OF ESTERIFICATION PROCEDURES

|  | Solvent-Free | DMF Solvent | NMP Solvent | Alkyl Acetate Solvent |
|---|---|---|---|---|
| Reaction Time (at 55° C. - excluding work up) | 7.5 hours | 17 hours | 17 hours | >20 hours |
| Waste Water BOD (biological oxygen demand - lbs. $O_2$/lb. product) | 0.25 | 1.2 (estimate) | 1.2 | <0.1 (estimate)* |
| Oil Repellency (0.25% application - 5 wash cycles) | 5-6 | 4-5 | 5-6 | 4-5 |

*Solvent must be distilled.

What is claimed is:

1. In a process for the esterification of a carboxyaromatic by reacting an anhydride of said carboxyaromatic with a fluorinated alcohol followed by reacting the remaining free carboxyl groups on said carboxyaromatic with an epoxide, the improvement which comprises utilizing said epoxide as the reaction medium for said esterification when said epoxide is a liquid under the reaction conditions employed.

2. The process of claim 1 wherein said fluorinated alcohol is employed in approximately stoichiometric quantities, and said epoxide is employed in an amount to provide about a 150 to 250% molar excess of epoxide over the amount required to react with the free carboxyl groups remaining after esterification by the fluorinated alcohol.

3. The process of claim 2 wherein the fluorinated alcohol is a (perfluoroalkyl) ethanol or (perfluoroalkyl) propanol having three to twelve carbon atoms in the perfluoroalkyl groups; or an (omega-perfluoroisopropoxy-perfluoroalkyl) ethanol or propanol having two to ten carbon atoms in the perfluoroalkyl groups.

4. The process of claim 3 wherein the fluorinated alcohol is a 2-(n-perfluoroalkyl) ethanol or a mixture of 2-(n-perfluoroalkyl) ethanols having six to twelve carbon atoms in the perfluoroalkyl group.

5. The process of claim 4 wherein the carboxyaromatic anhydride is selected from the group consisting of pyromellitic dianhydride and 3, 4, 3', 4'-benzophenone tetracarboxylic dianhydride.

6. The process of claim 5 wherein the epoxide is selected from the group consisting of epichlorohydrin and glycidol.

7. A process comprising intimately mixing pyromellitic dianhydride, a fluorinated alcohol consisting of a mixture of 2-(n-perfluoroalkyl) ethanols having six to twelve carbon atoms in the perfluoroalkyl groups, and epichlorohydrin, and heating said mixtures to form the tetraester of said pyromellitic dianhydride.

8. The process of claim 7 wherein about two moles of fluorinated alcohol and at least 5 moles of epichlorohydrin are employed per mole of pyromellitic dianhydride and the reaction is conducted at about 40°-60° C.

9. The process of claim 8 wherein about 5.5 to 6.5 moles of epichlorohydrin per mole of pyromellitic dianhydride are employed.

* * * * *

UNITED STATES PATENT AND TRADEMARK OFFICE
CERTIFICATE OF CORRECTION

PATENT NO. : 4,395,566
DATED : July 26, 1983
INVENTOR(S) : James H. Covill, Michael G. Kelly and Thomas F. Leahy It is certified that error appears in the above—identified patent and that said Letters Patent is hereby corrected as shown below:

On the title page, in the abstract line 4: "expoxide" should read "epoxide"

lines 6-7 "ex-poxide" should read "epoxide"

Signed and Sealed this

Eighth Day of November 1983

[SEAL]

Attest:

Attesting Officer

GERALD J. MOSSINGHOFF

Commissioner of Patents and Trademarks